(12) United States Patent
Ives et al.

(10) Patent No.: US 7,643,861 B2
(45) Date of Patent: Jan. 5, 2010

(54) TECHNIQUE FOR DESIGN, AND PLACEMENT, OF A SUBDERMAL AG—AG/CL BIOPOTENTIAL ELECTRODE

(75) Inventors: John Richard Ives, 6325 Rideau Valley Drive, Manotick, Ontario (CA) K4M 1B3; Susan Elizabeth Phelan, 6325 Rideau Valley Drive, Manotick, Ontario (CA) K4M 1B3

(73) Assignees: John Richard Ives (CA); Susan Elizabeth Phelan (CA)

( * ) Notice: Subject to any disclaimer, the term of this patent is extended or adjusted under 35 U.S.C. 154(b) by 394 days.

(21) Appl. No.: 11/333,101

(22) Filed: Jan. 17, 2006

(65) Prior Publication Data

US 2006/0161058 A1 Jul. 20, 2006

Related U.S. Application Data

(60) Provisional application No. 60/644,353, filed on Jan. 18, 2005.

(51) Int. Cl.
*A61B 5/04* (2006.01)
(52) U.S. Cl. ...................... 600/377; 600/396
(58) Field of Classification Search ................ 600/377, 600/396
See application file for complete search history.

(56) References Cited

U.S. PATENT DOCUMENTS 4,805,625 A   2/1989   Wyler
5,170,788 A * 12/1992  Blumenfeld ................ 600/372
6,053,173 A *  4/2000  Cary, III ..................... 128/898

OTHER PUBLICATIONS

Ives & Gloor, "New Sphenoidal Electrode Assembly to Permit Long-term Monitoring of the Patient's ICTAL or Interictal EEG", *Electroencephalography and Clinical Neurophysiology*, 1977, 42:575-580.
Ives & Gloor, "Update: Chronic Sphenoidal Electrode", *Electroencephalography and Clinical Neurophysiology*, 1978, 44:789-790.

* cited by examiner

*Primary Examiner*—Lee S Cohen
(74) *Attorney, Agent, or Firm*—Craig A. Fieschko, Esq.; DeWitt Ross & Stevens S.C.

(57) ABSTRACT

A chronic subdermal silver-silver/chloride (Ag—Ag/Cl) electrode for the recording of biopotentials is disclosed. The electrode is comprised of an Ag—Ag/Cl distal end that is placed subdermally by various methods. The recording electrode is made of solid, multi-stranded or a ball of pure silver and the whole length of the electrode is insulated except for the distal end which is used for voltage recordation. The electrode can be placed subdermally by an introducer apparatus such as hypodermic or sewing needle, a split-cannula, a staple, or a suture. Once placed, the introducer apparatus can be removed leaving the recording wire/element in place. The recording electrode can be placed at any location on the body to record the local biopotential (EEG, EOG, EMG, EKG, etc). It can be left in place for hours, days, or weeks, as it will record without any further adjustment.

14 Claims, 6 Drawing Sheets

TECHNIQUE FOR DESIGN, AND PLACEMENT, OF A SUBDERMAL AG—AG/CL BIOPOTENTIAL ELECTRODE

This utility patent application claims the benefit of Provisional Application No. US 60/644,353 filed Jan. 18, 2005.

FIELD OF THE INVENTION

The present invention relates to a subdermal silver-silver/chloride ("Ag—Ag/Cl") wire electrode ("SWE") for conveniently recording of any biopotential (EEG, EOG, EMG, EKG, etc.) by placing a pure silver wire with an Ag—Ag/Cl coated biopotential recording element using various methods in the subdermal (subcutaneous) space. One embodiment teaches the use of a hypodermic needle as an insertion tool to carry the SWE under the skin, immediately removing the hypodermic needle, leaving the recording wire/electrode in place as shown in the drawings (FIG. 1-5) disclosed herein. Another embodiment teaches the use of a sewing type needle that carries in the electrode, leaving the recording electrode behind when the sewing needle is removed as shown in the drawing (FIG. 6) disclosed herein. A further embodiment teaches the use of a stable or suture to place the Ag—Ag/Cl recording electrode. The SWE has been generally designed to record any biopotential chronically, specifically the EEG from patients in the ICU, OR, LTM (Long Term Monitoring, Epilepsy Units), where the assessment of neurological status over a chronic period of time is necessary. The SWE of the present invention can also be used to record long-term EKG signals for days and weeks without any electrode replacement or adjustment. Since the Ag—Ag/Cl recording surface can record DC, the electrode can be used for eye movement recordings (EOG) associated with sleep monitoring. The electrode is MRI and CT compatible and thus does not have to be removed before imaging. The electrode can be used to record any biopotential in animal research and veterinarian applications as it can be quickly inserted into the subject subdermally without shaving or surgery.

BACKGROUND OF THE INVENTION

Biopotential electrodes have been used for more than a century to record the electrical potential at the site of the electrode application. The most common electrode is the disc electrode that can be composed of almost any conducting material to promote low impedance and high quality of signal properties. These electrodes are easy to apply as they are either held in place with the conductive paste, glue, or a self-sticking media. They are considered to be an acute electrode as they eventually deteriorate in signal quality as the impedance increases or they become loose and fall off. This type of electrode needs to be replaced, or adjusted every 12-24 hours to ensure signal viability. One of the "best" surface, recording disc electrodes is the silver-silver/chloride type. However, a skill technician must apply the electrode after careful skin preparation. Eventually (usually between 12 and 24 hours), this electrode needs to be tended to, in order to apply more conductive jelly and reestablish a low impedance and signal integrity. The main disadvantages of the surface disc are: it requires placement, fixation and maintenance by a skill technician; it requires maintenance every 12-24 hours; and it is very susceptible to artifact.

Another type of electrode is the subdermal needle electrode, which is usually composed of a solid metal (such as tungsten, stainless steel, platinum, etc.). It can be inserted subdermally and provides an immediate biopotential signal. The quality of the recording is reasonable but they are prone to artifact and usually have high impedance. They are usually considered to be acute electrodes (minutes, hours) as their rigid properties limit their application on freely moving subjects. Their main disadvantages are: they are a rigid electrode that can cause injury; they are prone to movement and other forms of artifact due to the rigidity and high impedance; and they are acute electrodes.

Several years ago, workers in the EMG field used hypodermic needles to insert stainless steel wires into the muscle to permit acute EMG recordings. Later, in a specific application, this technique was modified by Ives and Gloor in 1977 (Ives, J. R. and Gloor, P. New sphenoidal electrode assembly to permit longterm monitoring of the patient's ictal and interictal EEG. *Electroenceph. Clin. Neurophysiol,* 1977; 42:575-580) to place a chronic sphenoidal recording electrode in order to record the patient's EEG from the area of the mesial temporal lobe. Wyler then further modified this technique as taught in U.S. Pat. No. 4,805,625 (issued Feb. 21, 1989).

The present invention discloses a Ag—Ag/Cl electrode element that can be of any shape or size (solid, stranded wire, ball of pure silver with a silver-silver/chloride coating) depending on the application. Specifically as an example, a multi-stranded, Teflon insulated, silver wire with a silver-silver/chloride recording tip can be placed subdermally at any body location (human or animal) where one desires to chronically record a biopotential. The insertion device, or introducer, can be a hypodermic or sewing needle, split-cannula, a staple, or a suture. As an example, the multi-stranded pure silver wire with a Ag—Ag/Cl recording tip electrode can be placed by hand using a hypodermic needle as taught by Ives in 1977, 1978 and 2005 (Ives, J. R. and Gloor, P. New sphenoidal electrode assembly to permit longterm monitoring of the patient's ictal and interictal EEG. *Electroenceph. Clin. Neurophysiol,* 1977; 42:575-580; Ives, J. R. and Gloor, P. Update: sphenoidal. *Electroenceph. Clin. Neurophysiol,* 1978; 44:789-790; Ives, J. R. New Chronic EEG Electrode for CCU/ICU Monitoring. *J. Clin. Neurophysiol,* 2005; 22:119-123.) and Wyler (supra).

SUMMARY OF THE INVENTION

It is an object of the present invention to provide an improved chronic, biopotential electrode.

It is another object of the present invention is to provide different shapes and forms of a biopotential electrode.

Another object of the present invention is to provide a semi-automatic apparatus and method for the placement of the biopotential electrode in the subdermal space just under the skin of an animal or human in order to record the biopotential electrical field located at that point.

A further object of the present invention is to provide an "ideal electrode" recording surface in the form of a silver-silver/chloride coating on the active recording surface of the biopotential electrode.

All of the above objects are in part to achieve the recording advantages of a Ag—Ag/Cl coated electrode that overcomes problems, disadvantages, and shortcomings of the prior art; namely with surface disc and subdermal needle electrodes.

Accordingly, the present invention provides an improved Ag—Ag/Cl coated biopotential electrode, apparatus and method for the subdermal placement of the chronic, Ag—Ag/Cl coated biopotential, chronic recording electrode. The subdermal Ag—Ag/Cl biopotential electrode is comprised of a pure multi-stranded or solid silver wire having proximal and distal ends; wherein the wire is substantially coated with Telfon. The distal end is Telfon-free and this Telfon-free distal end is electrolysed with silver/chloride. The proximal end of the wire is connected to a biopotential voltage recording means.

BRIEF DESCRIPTION OF THE DRAWINGS

The invention will be better understood and objects other than those set forth above will become apparent when consideration is given to the following detailed description thereof. Such description makes reference to the annexed drawings wherein.

DETAILED DESCRIPTION OF THE PREFERRED EMBODIMENT

The preferred embodiment of the subdermal biopotential electrode of the present invention comprises the Ag—Ag/Cl wire electrode itself, the introducer or insertion apparatus and the protective cap.

The electrode is comprised of pure (99.9%) multi-stranded or solid Teflon insulated silver wire. The recording area is at the distal end of the wire which is bared for about 3-4 mm and then this exposed area is coated with an electrolysis process with silver/chloride to therefore form an "ideal" silver-silver/chloride, biopotential, recording electrode. Other coatings can be added to improve the stability of the Ag—Ag/Cl surface. The proximal end of the wire is connected to a simple connector to allow a quick and easy connection to any recording/monitoring apparatus.

The introducer apparatus can be a hypodermic needle, a split-cannula, a staple, or a suture that is used to facilitate and place the Ag—Ag/Cl coated electrode in the subdermal space.

Once inserted subdermally, the wire electrode can be held in place with tape, glue or a wrap; while the connector can be plugged into a remote recording/monitoring apparatus. The electrode can record the biopotential for hours, days or weeks without any further adjustment. It can be easily and quickly removed by first reversing the holding method and exerting a steady pull in line with the axis of the wire, or using a staple, suture removal kit.

The silver wire is generally malleable enough to readily unfold and slip out.

Preferably, a ⅝", ultra thin-wall 25-gauge hypodermic needle is used as the introducer apparatus.

Preferably, a 2" piece of Teflon coated pure silver wire with an overall diameter of about 0.0045" or 0.114 mm is used as the recording electrode wire.

Preferably, about 3 to 4 mm of Teflon is stripped from the distal recording tip. This tip is then placed in chlorine bath with a silver anode while 1.5 Volts is applied for about 15 minutes to achieve a silver-silver/chloride recording tip.

Details of the preferred embodiment will now be described with reference to the drawings.

Figure 1:
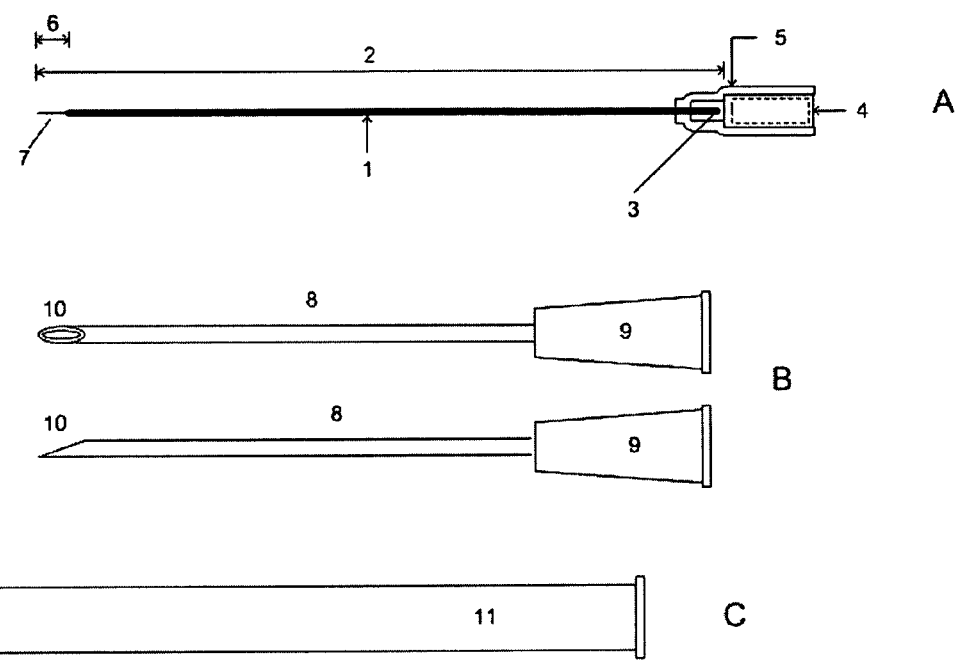
FIG. 1 shows the three parts of the wire electrode apparatus, namely Part A—the wire electrode itself, Part B—the insertion needle and Part C—the protective sheath.

As shown in the accompanying drawings, Part A of FIG. 1 describes an improved biopotential recording electrode. This electrode shown is comprised of a length of pure silver, Teflon coated wire 1. The distal tip of the wire is bared of its Teflon insulation 6 for approximately 3 mm to form an exposed surface of pure silver. This surface is then coated in silver-chloride to form an "ideal" recording electrode. This recording electrode tip 7 can then be placed about 10 to 15 mm subdermally to permit recording of the biopotential voltage situated at that point. The proximal end of the wire electrode 1 can be soldered or crimped 3 to the connector element 4 which permits external connection to a recording device via an extension wire. This connector 4 is insulated and sealed with heat-shrink tubing 5. Optionally, an on-head preamplifier/multiplexer unit with mass connectors can be used to record the signals. The mass-connector permits simple, accurate and quick disconnect and reconnect by nursing staff.

Part B of FIG. 1 illustrates a hypodermic needle 8 shown in two views. The sharp end lumen 10 of the hypodermic needle 8 has a slanted bevel to permit penetration of the skin and allows the needle to carry in the wire electrode's recording tip 7 in order to place the tip of the wire 7 in the subdermal space. The proximal end of the needle 8 is a hub 9 for easy grasping of the needle.

Part C of FIG. 1 shows a protective cap 11 for placement over the needle/wire assembly (Parts A & B) to form a complete unit (Parts A, B & C).

Figure 2:
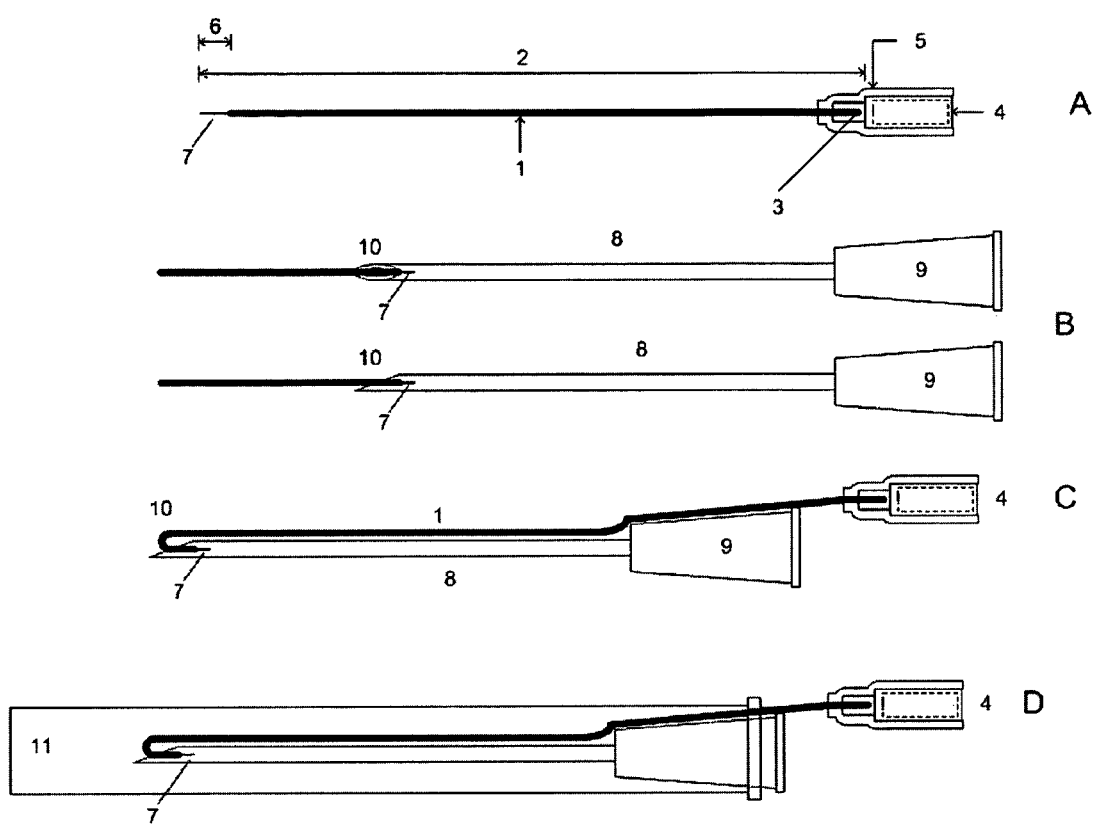
FIG. 2 shows the details of the wire electrode and the placement of the recording tip into the lumen of the insertion needle, the folding back over the needle and the replacement of the protective sheath.

Referring now to Part B of FIG. 2 where the tip of the wire electrode 7 is shown as placed into the lumen 10 of the hypodermic needle 8. In Part C, the wire electrode 1 is folded back along the sheath of the needle 8. Finally the protective cap 11 is placed over the needle/wire assembly as shown in Part D.

Figure 3:
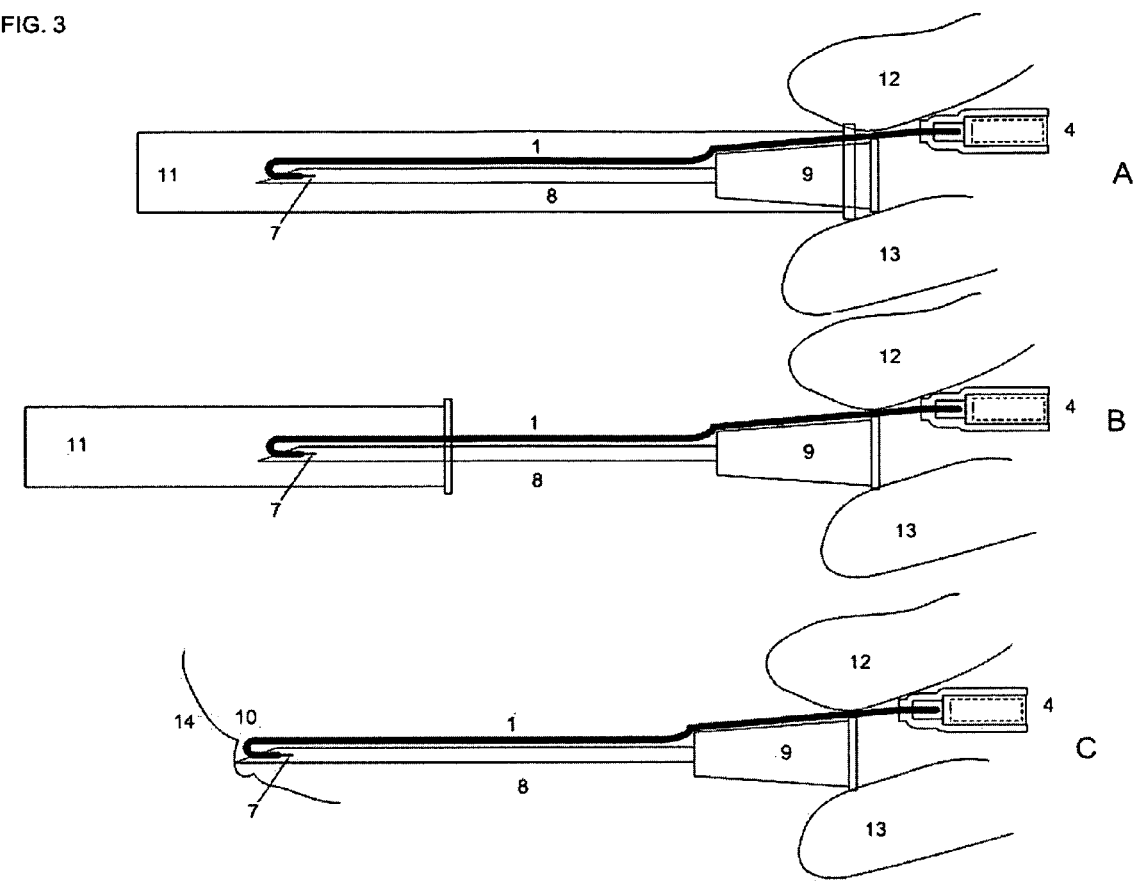
FIG. 3 shows the technique for preparing the subdermal wire electrode for placement in the subdermal space.

In FIG. 3, Part A, a user grasps the needle hub 9 and wire assembly between the index finger 12 and the thumb 13 to permit removal of the protective cap 11 in preparation for inserting the tip 7 subdermally (see Part B). In Part C, the tip 10 of the hypodermic needle 8 carrying the wire electrode 7 is shown pressed up against the skin 14 ready to penetrate into the subdermal space.

Figure 4:
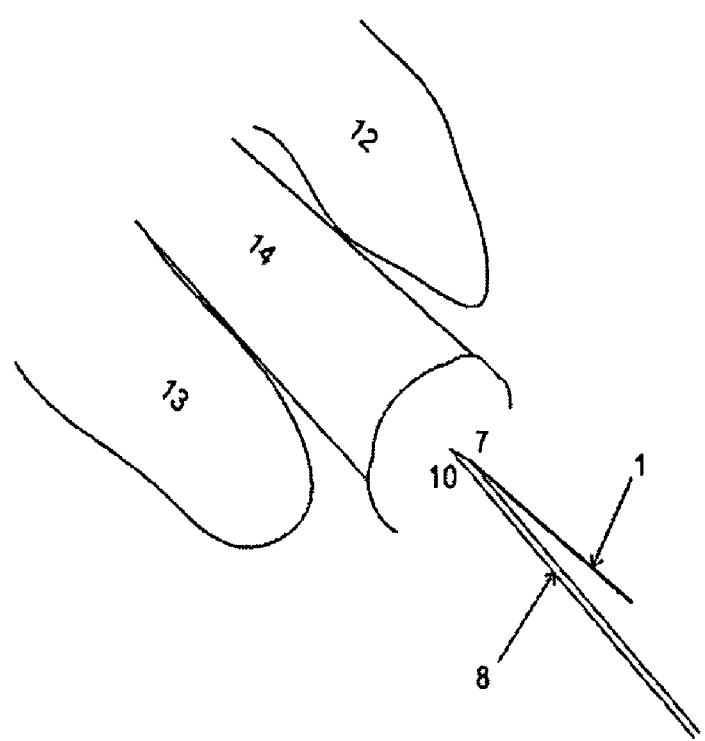
FIG. 4 shows the method of placing the wire electrode and introducer against a furrow of skin before inserting the wire and introducer into the subdermal space.

FIG. 4 demonstrates the insertion of recording element tip 7 subdermally with the assistance of an introducer, in this case a hypodermic needle 8. A furrow of skin 14 can be grasped between the index finger 12 and thumb 13 of the opposite hand to permit the tip 10 of the hypodermic needle 8 carrying the recording wire 1 and the recording element tip 7 into the subdermal space.

Figure 5:
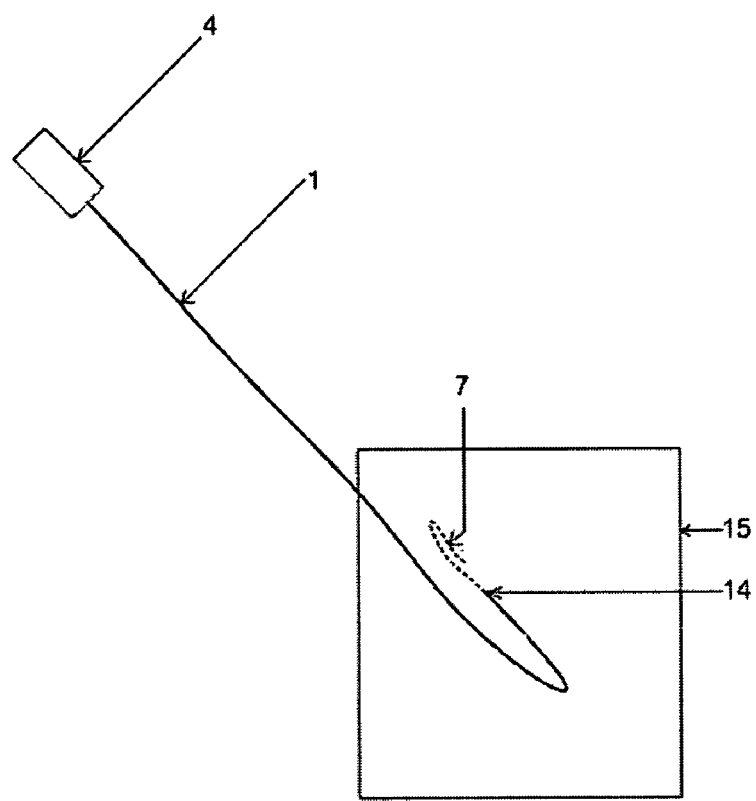
FIG. 5 shows the subdermal wire electrode placed in the subdermal space and the removal of the needle introducer. A holding device has now been placed over the wire and the point of insertion into the subdermal space.

FIG. 5 shows the subdermal placement of the electrode recording tip 7 under the skin 14 and the length of the recording wire 1 and the connector 4. A holding down adhesive 15 such as tape, gauze, or glue can be applied on the surface of the skin 14 to hold the wire and the electrode securely in place.

Figure 6:
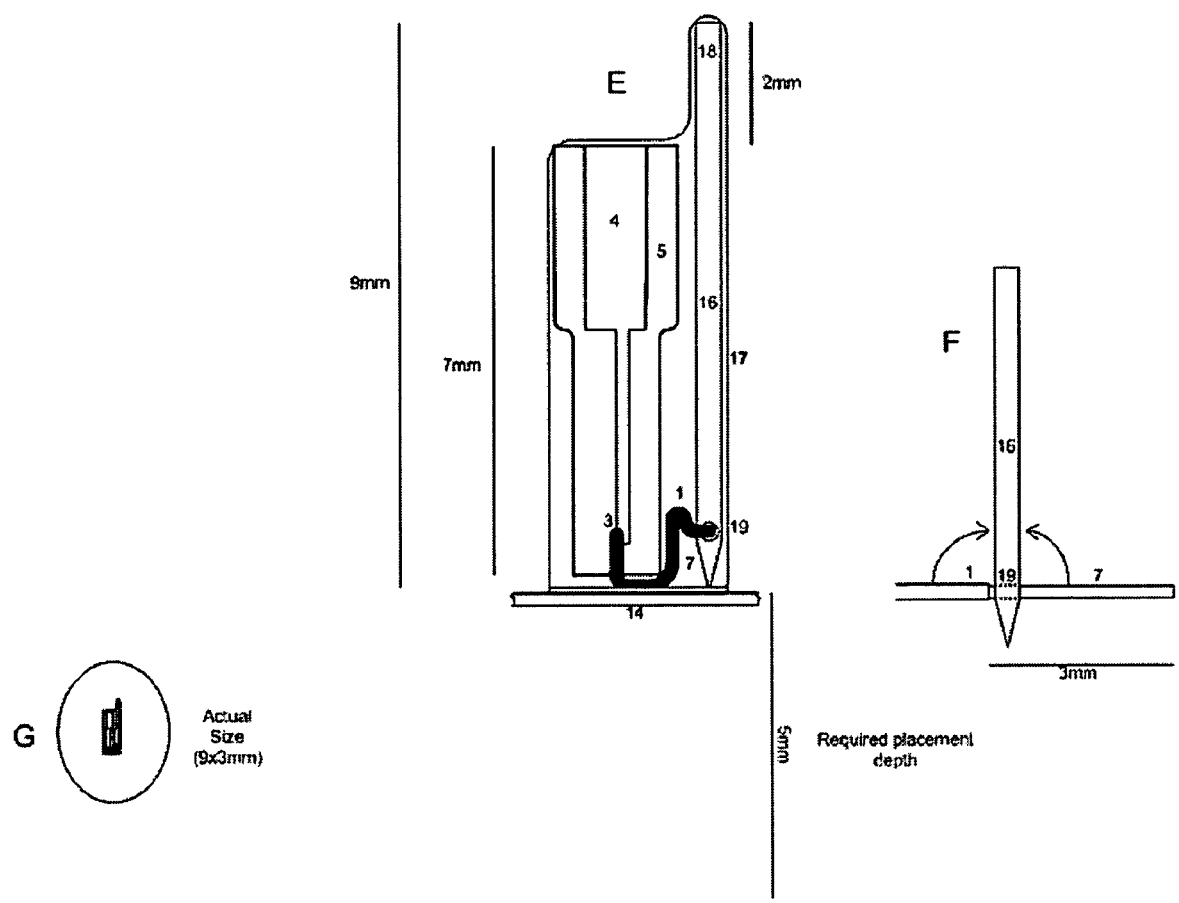
FIG. 6 is a representation of a semi-automatic SWE injection package containing the injection device and the wire electrode.

FIG. 6 illustrates a self-contained subdermal wire electrode unit 17 ready to be grasped by a protrusion or latching element or extension 18 which permits external gripping or attachment of a semi-automatic device for placement on the skin 14 and allowing for the wire to be injected into the subdermal space. In this example, a sewing type needle 16 with a through hole or "eye" 19 is used to hold the wire 1 and the bared recording tip 7 as shown in view E. View F shows the arrangement turned 90 degrees. View G shows the approximate actual size of the unit 17. In the embodiment shown, the wire 1 is just long enough to permit it to be self extracted from the "eye" 19 of the needle when it is at the correct depth in the subdermal space. The connector 4 and insulation element 5 attached to the recording wire at 3 is then ready to have an extension wire attached to allow the biopotential voltage to be recorded by a remote recording device.

Thus, in accordance with this above-illustrated embodiment, a separate unit picks up the self-contained SWE, sterilized package (wire electrode pre-treaded through the "eye" of a needle). Once positioned over the desired area for injecting the SWE, the apparatus is activated and it places the subdermal wire electrode just under the skin. The needle is then extracted. The SWE is now ready to record.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A wire electrode for measuring biopotentials in a subdermal layer, said electrode comprising a pure multi-stranded or solid silver wire, said wire being insulated and having an uninsulated distal end, the uninsulated distal end of said wire being at least 3 mm in length and coated with silver/chloride, a proximal end of said wire being operatively coupled to a biopotential recording device.

2. The wire electrode of claim 1, wherein said proximal end of said wire further comprises a connector for operatively coupling same to said biopotential voltage recording device.

3. The wire electrode of claim 2, wherein said connector is insulated and sealed with heat-shrink tubing.

4. The wire electrode of claim 2, wherein said connector is soldered or crimped to the proximal end of the wire.

5. The wire electrode of claim 1, wherein the pure multi-stranded or solid insulated silver wire has a length of 2" and an overall diameter of about 0.0045" or 0.114 mm.

6. The wire electrode of claim 1, wherein the distal end of the wire is 3 mm in length.

7. The wire electrode of claim 1, wherein the distal end of the wire is coated with silver/chloride by placing the distal end of the wire in chlorine bath with a silver anode with a voltage potential of 1.5 Volts for about 15 minutes.

8. The wire electrode of claim 1, wherein said wire is chlorided with a silver salt to enable recordation of biopotential voltage at the site of placement for EEG, EGG, EKG, EMG applications.

9. The wire electrode of claim 1, wherein the distal end of the wire is 4 mm in length.

10. The wire electrode of claim 1, wherein said proximal end of the wire is operatively coupled to a biopotential recording device via an extension wire.

11. An electrode device for introducing a wire electrode in a subdermal layer and measuring biopotentials therein, said electrode device comprising: a wire electrode comprising a pure multi-stranded or solid silver wire, said wire being insulated and having an uninsulated distal end, the uninsulated distal end of said wire being at least 3 mm in length and coated with silver/chloride, a proximal end of said wire being operatively coupled to a biopotential recording device, an introducer needle for introducing the distal end of the wire in the subdermal layer, said introducer needle comprising a needle hub and a hollow needle extending therefrom, said hollow needle being at least 25 gauge, whereby the wire is hooked into a needle lumen of the hollow needle at the distal end of the wire and the wire is folded back along the length of the hollow needle to carry the distal end of the wire into the subdermal layer.

12. The electrode device of claim 11, wherein said hollow needle is ⅝" in length.

13. The electrode device of claim 11, wherein said hollow needle has a sharp end lumen and a slanted bevel for permitting penetration of the skin and for allowing said hollow needle to carry the distal end of the wire to the subdermal layer.

14. The electrode device of claim 11, further comprising a protective cap for placement over the introducer needle and a portion of the wire electrode.

\* \* \* \* \*